(12) United States Patent
Efinger et al.

(10) Patent No.: US 8,721,806 B2
(45) Date of Patent: May 13, 2014

(54) DEVICE FOR CLEANING A FLEXIBLE HOLLOW SHAFT OF A MEDICAL INSTRUMENT

(75) Inventors: Andreas Efinger, Rietheim (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 927 days.

(21) Appl. No.: 11/686,869

(22) Filed: Mar. 15, 2007

(65) Prior Publication Data
US 2007/0215190 A1 Sep. 20, 2007

(30) Foreign Application Priority Data
Mar. 15, 2006 (DE) .................. 10 2006 013 980

(51) Int. Cl.
*B08B 9/00* (2006.01)
(52) U.S. Cl.
USPC ...................................... 134/166 R
(58) Field of Classification Search
USPC ...................................... 134/166 R
See application file for complete search history.

(56) References Cited

U.S. PATENT DOCUMENTS

| | | | |
|---|---|---|---|
| 5,279,317 A | 1/1994 | Bowman et al. | 134/166 |
| 6,044,855 A | 4/2000 | Moench | 134/169 |
| 6,824,751 B2 | 11/2004 | Rossell | 422/295 |
| 2003/0032970 A1* | 2/2003 | Hiltebrandt | 606/170 |
| 2004/0118440 A1 | 6/2004 | Sasaki et al. | 134/166 |

FOREIGN PATENT DOCUMENTS

| | | |
|---|---|---|
| DE | 196 46 584 | 4/1998 |
| EP | 0 986 989 | 3/2000 |
| EP | 1 398 004 | 3/2004 |

OTHER PUBLICATIONS

European Search Report, Jul. 30, 2007, 7 pages.

* cited by examiner

*Primary Examiner* — Jason Ko
(74) *Attorney, Agent, or Firm* — St. Onge Steward Johnston & Reens LLC

(57) ABSTRACT

A device is used for cleaning a flexible hollow shaft of a medical instrument, the wall of said flexible hollow shaft is provided with openings. The device comprises a hollow space in which at least one portion of said hollow shaft can be received. A cleaning liquid can be delivered into said hollow space via an attachment piece. An inside wall of said hollow space is at a radial distance from the outer face of said hollow shaft. Flow resistance means, spaced axially apart from one another, are provided, either in the form of sealing means or in the form of narrow annular gaps which respectively seal off or delimit, in the axial direction, a space between said outer face of said hollow shaft and said inside wall of said hollow space.

21 Claims, 10 Drawing Sheets

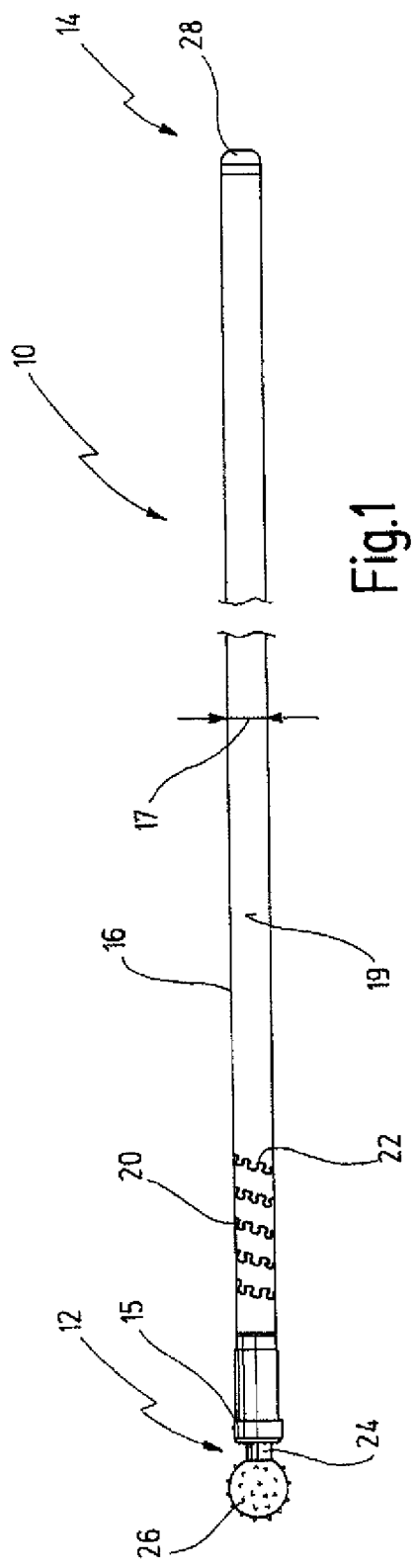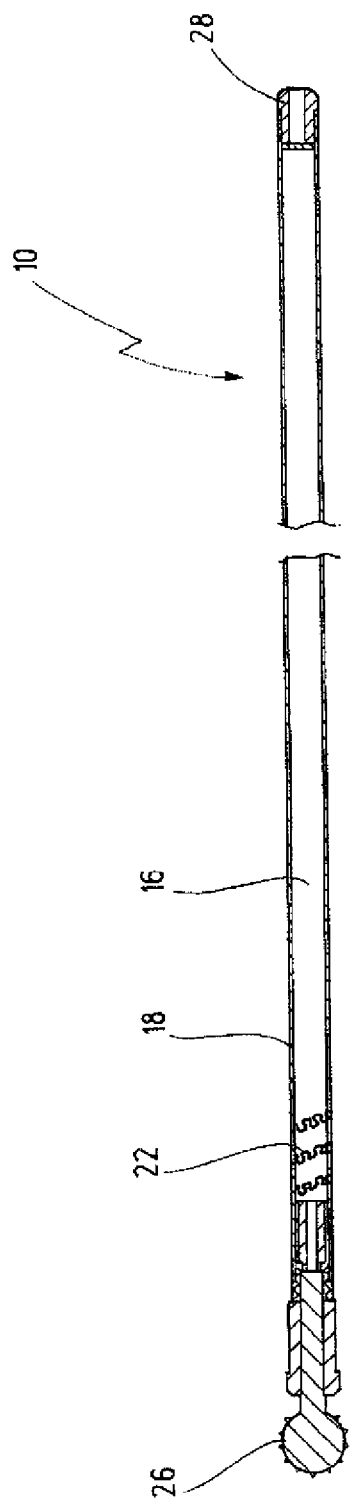

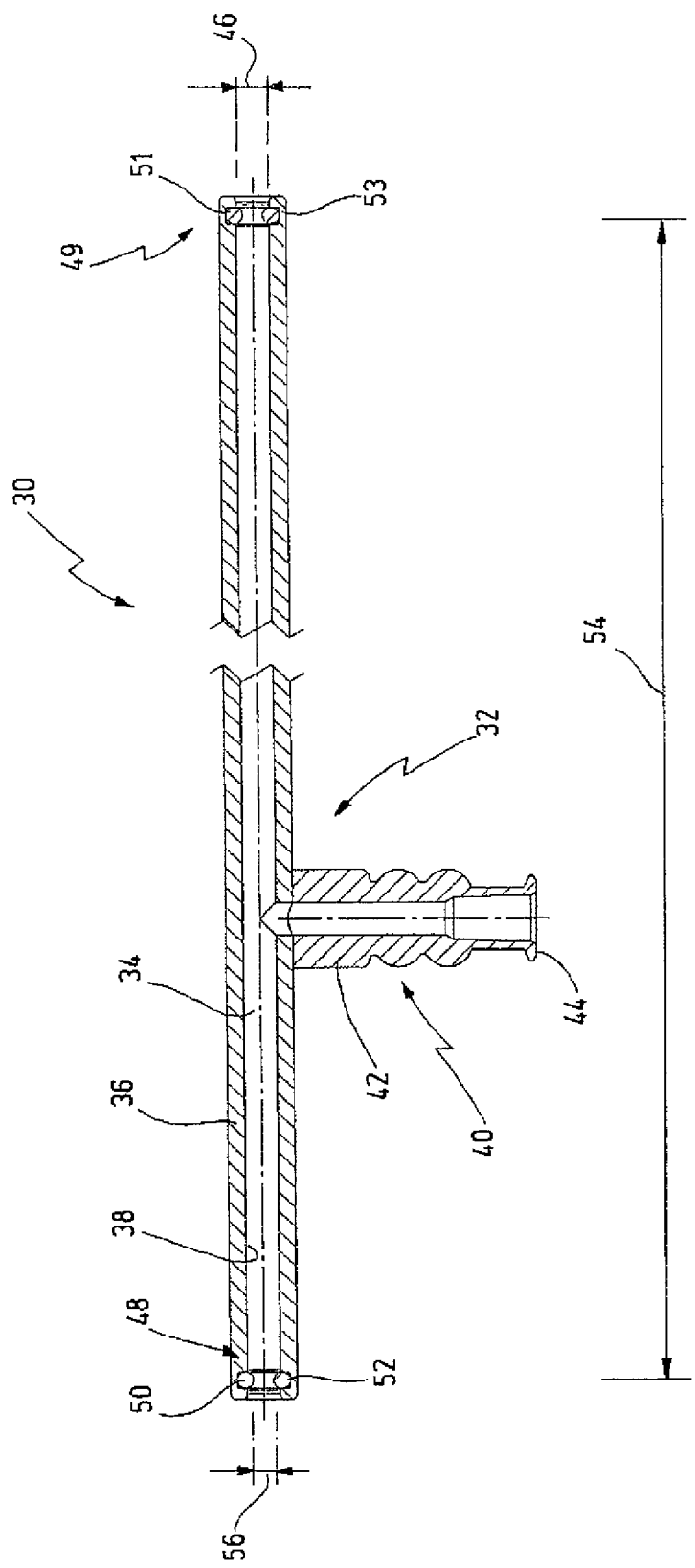

DEVICE FOR CLEANING A FLEXIBLE HOLLOW SHAFT OF A MEDICAL INSTRUMENT

BACKGROUND OF THE INVENTION

The invention relates to a device for cleaning a flexible hollow shaft of a medical instrument, the wall of which flexible hollow shaft is provided with openings.

A surgical instrument having a flexible hollow shaft of this kind is known from EP 0 986 989 A1.

The flexibility of the hollow shaft means that the instrument can have a curved design. The flexible hollow shaft is received in the curved instrument shank and its proximal end is connected to a drive mechanism which rotates the hollow shaft in the curved instrument shank. At the distal end, the hollow shaft is provided with a tool, for example a cutting edge or a milling head. The wall of the hollow shaft is provided either with a single winding opening or with a large number of openings, by which the flexibility is achieved. This opening consists, for example, of a meandering cut made in the wall and extending along a helical line. In this way, with a curved and rotating hollow shaft, it is possible for the openings on the outer face of the curvature to widen slightly.

As has been mentioned before, the hollow shaft in the medical instrument is used for removing tissue from a body or for milling a bone. Contaminating liquids such as blood or other tissue fluids come into contact with the hollow shaft. By way of the openings or slits in the wall of the hollow shaft, these contaminating liquids can penetrate into the interior of the hollow shaft.

When cleaning the hollow shaft, the latter is usually detached from the instrument and stretches out in a straight line.

For cleaning the hollow shaft, it is not just its inner and outer faces that have to be cleaned, but also the openings, in particular the meandering slits, the width of which is in the range of approximately 0.05 to 1 mm.

This has proven extremely awkward and difficult in practice.

It is therefore object of the present invention to provide a device for cleaning a flexible hollow shaft in a simple and effective way.

SUMMARY OF THE INVENTION

According to the invention, the object is achieved by a device containing a body which has a hollow space and in which at least one portion of the hollow shaft can be received, wherein a cleaning agent can be delivered into the hollow space via an attachment piece, an inner wall of the hollow space is at a radial distance from the outer face of the hollow shaft, and flow resistance means spaced axially apart from one another are provided which delimit, in the axial direction, a space between the outer face of the hollow shaft and the inside wall of the hollow space.

A hollow shaft that is to be cleaned can be inserted into a device having these structural features. Since the radial diameter of the hollow space in the interior of the body is greater than the external diameter of the hollow shaft, a space exists all around the outer face of the hollow shaft, and this space can be supplied from outside with a cleaning agent via the attachment piece. The provision of axially spaced apart flow resistance means, which axially delimit this space from the outside, has the effect that the delivered cleaning agent can pass through the openings in the wall of the hollow shaft and into the interior thereof. The flow resistance means extend in a radial direction and delimit a flow of said cleaning fluid in an axial direction beyond said flow resistance means. In this way, not only the outer face of the portion of the hollow shaft received in the hollow space of the body is cleaned, but also the openings or slits are cleaned, by the cleaning agent penetrating inward from outside into the hollow shaft. By suitable pressurization of the cleaning agent, the flow resistance of the in most cases meander-like slits can be suitably overcome. The cleaning agent passing into the interior of the hollow shaft is then conveyed out of the hollow shaft, either at the ends of the hollow shaft protruding from the device, or via special openings which are provided in the wall of the hollow shaft and which lie axially outside the flow resistance means. Not only are the contaminants carried away by this means, the inner face or inside wall of the hollow shaft is also cleaned at the same time.

The cleaning agent can be a cleaning liquid. It can also be delivered in the form of gases, e.g. cleaning air. It is also possible to deliver mixtures of a carrier and a cleaning agent, irrespective of their state of aggregation.

By means of the device according to the invention, a portion of the hollow shaft can now be completely cleaned, i.e. its outer face, the apertures in the wall, and its inside. This ensures particularly simple and effective cleaning of such a hollow shaft, particularly in the area of its apertures, since at these locations the cleaning agent flows radially inward from the outside and flushes contaminating liquids or other contaminants away.

In an embodiment of the invention, the body of the device is designed as a hollow cylinder.

This measure has the advantage that the device forms a slender structure into the interior of which the hollow shaft can be inserted for cleaning. This can be done very easily and also facilitates the cleaning procedure.

In another embodiment of the invention, the body extends in a straight line.

In this embodiment, the hollow shaft is correspondingly elongate, and the openings in its wall (in most cases the meandering, helically extending slits cut by a laser beam) have constantly the same width, such that the inflowing cleaning agent encounters a uniform flow resistance, which has the effect that the cleaning agent passes in a uniformly distributed manner through the openings and into the interior of the hollow shaft.

In another embodiment of the invention, the body extends in a curved shape.

A curved body of the device has the advantage that, in the outer periphery of the curvature, the openings or slits of the hollow shaft are slightly spread, such that the inflowing cleaning agent encounters slightly less resistance in this area. However, the hollow shaft should then be rotated in the device to ensure that all the slits are cleaned uniformly.

This design may be desirable if there is a danger that very small and fine particles may become caught in the slits and cannot be flushed out from the slits by the pressure of the cleaning agent, for example if these fine particles have a wedge-shaped contour. It is then helpful if the slits in the curved body are at least temporarily spread out slightly, such that adhering solid particles can likewise be flushed off into the interior. This is especially helpful if the tool of the hollow shaft is designed as a milling head.

In another embodiment of the invention, the axial distance between the flow resistance means corresponds approximately to the length of the portion of the hollow shaft provided with the openings.

This measure has the advantage that almost all the openings along the lengthwise portion of the hollow shaft can be cleaned in a single operating procedure.

In one embodiment of the invention, the flow resistance means are designed as sealing means.

This measure has the advantage that the cleaning agent delivered via the nozzle into the space between the inside wall of the hollow space and the outer face of the hollow shaft must pass in its entirety through the wall of the hollow shaft. By designing the flow resistance means as sealing means, axial escape of the cleaning agent between the outer face of the hollow shaft and the inside of the hollow space in the axial direction is prevented, i.e. delimited to zero. Since the sealing means at the sealing locations are in leaktight contact with the outer face of the hollow shaft that is to be cleaned, cleaning at these locations is possible only if the position of the hollow shaft during the cleaning procedure is changed at least once, such that locations initially occupied by the sealing means can likewise be cleaned.

In another embodiment of the invention, the attachment piece for delivery of the cleaning agent is arranged approximately centrally in the body.

This measure has the advantage that the body of the hollow shaft provided with openings can be permeated uniformly on both sides of the attachment piece, and pressure losses in the axial direction are negligible.

In another embodiment of the invention, the hollow shaft is displaceable relative to the body.

This relative displaceability can be achieved by the fact that either the body is stationary and the hollow shaft is displaced in the body, or vice versa, namely that the hollow shaft is stationary and the body is displaced over it, or that both are displaced.

This is desirable in particular if relatively long hollow shafts are to be cleaned and if the cleaning device, for stowage reasons or for other reasons, is to have only a relatively short axial extent.

In this case, for example, the hollow shaft is inserted into and pushed through the body such that only a certain partial section of the hollow shaft is received in the device. Since, in the case of seals, these seal off the section from the outside, the cleaning agent can penetrate into the interior of the hollow shaft only within this delimited section. By means of the relative displacement, the entire axial lengthwise section can now be successively supplied with the cleaning agent and cleaned, this being achieved by the aforementioned relative displacement.

In another embodiment of the invention, the axial distance between the sealing means is variable.

This measure has the advantage that, depending on the design of the hollow shaft and on the available pressurization of the cleaning agent, different axial sections can be cleaned.

In another embodiment of the invention, the sealing means are designed as O-rings.

This measure has the advantage that inexpensive and effective sealing means are provided for sealing off the space between the outer face of the hollow shaft, which is in most cases cylindrical, and the interior of the body of the device. The design as an O-ring also very easily permits the relative displaceability between device and hollow shaft and the mutual displaceability of the sealing means in the axial direction.

In another embodiment of the invention, the sealing means are received in axially displaceable bearing bushings.

This measure has the advantage that, by way of these bearing bushings, the axial spacing of the sealing means from one another can be varied.

For this purpose, the bearing bushings that hold the sealing means, for example the O-rings, are received axially displaceably in the interior of the body.

This displaceability can be effected mechanically from the outside by hand, for example if sections of different length of a hollow shaft are to be cleaned, or the displaceability can be achieved by regulating the pressure of the flushing liquid.

This opens up the possibility of the sealing means, at the start of a flushing procedure, being arranged at a relatively short axial distance from one another, and of the cleaning agent being initially introduced in this state. The pressure can then be chosen such that part of the pressure applied to the cleaning agent serves to displace the sealing means in opposite axial directions, so that, gradually, an increasingly larger section of the body of the hollow shaft is flushed through.

This shows the flexible design of the device according to the invention, so that it can be adapted to different designs and shapes of hollow shafts.

In another embodiment of the invention, the flow resistance means are created by means of the fact that the radial distance of the inner wall of the hollow space from the outer face of the hollow shaft is smaller in the area of the flow resistance means than it is in the area between these axially spaced apart locations.

This measure has the advantage that, unlike the previously described situation, there is not now a complete sealing at the axially spaced apart locations, and instead the flow resistance means are formed by a radially narrowed space.

This affords the possibility that some of the cleaning agent can also pass axially through this area of the radially narrowed space between the inside of the hollow space and the outer face of the hollow shaft and thus escape. It is thus also possible to transport cleaning agent through this area of the flow resistance means and clean the outside. In this way, it is also possible to operate the device such that no relative displacement is needed between hollow shaft and device, since the cleaning agent can flow across the entire outer face of the hollow shaft. If an opening of the wall lies in this area, the cleaning agent can pass in the radial direction through the wall and clean the opening.

In another embodiment of the invention, this is achieved in design terms by the fact that, in the area of a flow resistance means, an annular gap is present between the inside wall of the hollow space and the outer face of the hollow shaft, and cleaning agent can pass axially through this annular gap.

This measure has the advantage that such an annular gap presents a precisely defined geometrical size, giving the cleaning agent a precisely defined and calculable flow resistance. This geometry also permits a self-centering of the hollow shaft in the annular gap, since the pressurized cleaning agent passing through the annular gap will flow through the annular gap in a uniformly distributed manner, as a result of which the centering is achieved. It is thus ensured that all areas of the outer face of the hollow shaft that come to lie in the region of an annular gap are supplied with cleaning agent flowing through them and are flushed.

In another embodiment of the invention, cleaning agent can additionally be delivered directly to the radially narrowed space, for example the annular gaps.

Given the normal sizes of such hollow shafts, the widths of the annular gaps are in the region of fractions of millimeters.

If a hollow shaft contaminated on its outer face is inserted into a device, it is not possible to exclude the possibility of contaminants, such as blood, tissue or bone chips, being pushed into this gap, i.e. the space between the outer face of the hollow shaft and the narrowed inside of the hollow space, and becoming caught there. It is also possible, during operation, that the parts flushed away in the area of larger diameter of the hollow space between the axially spaced apart locations will be moved in the axial direction along the outer face, pass into the annular gaps and block them at certain peripheral areas or even block them completely.

By affording the possibility of delivering cleaning agent directly to these annular gaps, they can be flushed free of such contaminants.

In another embodiment, this is very simply achieved in design terms by the fact that at least one bypass, branching off from the attachment piece, opens out in the area of an annular gap.

It is thus possible for some of the cleaning agent delivered to the device to be constantly branched off via the bypass and to be delivered directly and under pressure to the annular gap through the bypass and additionally from outside, as a result of which it is also possible for contaminants to be flushed away.

In another embodiment of the invention, a hollow shaft to be cleaned can be introduced into the hollow space only from a first end.

In the designs with the annular gaps, this measure proves to be advantageous in that particularly the annular gap at the insert end is exposed to the above-described contaminants, so that it then suffices to provide the additional design features of a bypass at one end, namely this insertion end.

In another embodiment of the invention, the first end is provided with a limit stop onto which a corresponding abutment of a hollow shaft can be placed.

This measure has the advantage that a precisely defined position of the hollow shaft relative to the body of the device is predetermined, such that the aforementioned flushing procedures via the annular gap can take place without any problem. This also affords the possibility of pushing the hollow shaft so far into the device that all the slits present in the wall of the hollow shaft lie in the interior of the hollow space, such that with a single flushing procedure, and in a single relative position between device and hollow shaft, the latter can be completely cleaned. This permits a fully automatic operation, so that initially the hollow shaft simply has to be inserted into the device as far as the limit stop, and then this assembly can be placed in an automated washing installation and supplied with cleaning agent.

In another embodiment of the invention, a distal end of the hollow shaft comes to lie on the first side.

This measure has the advantage that the hollow shaft is first inserted with the proximal area, which is in most cases less contaminated, from the first side. After complete insertion of the hollow shaft, the much more strongly contaminated distal area of the hollow shaft comes to lie at the first side and can be cleaned particularly thoroughly there.

In another embodiment of the invention, the body, on a second side lying opposite the first side, has an opening in the area of which the proximal end of the hollow shaft comes to lie.

This measure has the advantage that cleaning agent can also escape in the area of the second end. Depending on the design, that is to say with annular gaps or with sealing means, the cleaning agent that escapes via this opening is cleaning agent that has penetrated only into the interior of the hollow shaft, or additionally cleaning agent that is guided along the outer face of the hollow shaft via the annular gap.

In another embodiment of the invention, the body, at least in the area of the first side, is provided on its outer face with liquid-conducting features which ensure that cleaning liquid that strikes the outer face is delivered in a targeted manner to the first side.

This measure has the advantage that the first side, that is to say the insertion side, is supplied additionally with cleaning liquid which strikes the outside of the device, for example if the latter is received in an automatic washing machine provided with spray arms.

The hollow shaft has to be inserted from one side of the device. Irrespective of whether the flow resistance means are designed as sealing means or as annular gaps, quite large areas of contaminants adhering to the outer face of the hollow shaft are displaced along the outer face of the hollow shaft to the trailing end during insertion. This can lead to such contaminants accumulating in the area of the insertion side of the device. By means of the targeted delivery of the cleaning liquid from the outside to this location, such outer areas of adhering contaminants can be flushed completely away.

In another embodiment of the invention, the hollow space contains, at a distance from its inside wall, a partition wall which lies at a distance from the outer face of the hollow shaft, and through-openings are provided in the partition wall.

This measure has the advantage that the cleaning agent can be delivered, through the openings in the partition wall, in a very targeted manner to the outer face of the hollow shaft. In the embodiments in which the flow resistance means are designed as narrow annular gaps from which cleaning agent can flow out, the provision of openings in this area means that cleaning agent can be delivered in a particularly targeted manner. The cleaning agent flows from outside initially into the outer hollow space between the inside of the hollow space and the inside wall and can distribute itself uniformly there. As has been mentioned above, the cleaning agent is then delivered in a targeted manner through the openings in the inside wall and into the inner hollow space in which the hollow shaft is arranged.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which:

FIG. 1 shows a side view of a hollow shaft which is intended to be cleaned using the device according to the invention, FIG. 2 shows a longitudinal section of the hollow shaft from FIG. 1, FIG. 3 shows a longitudinal section of a first illustrative embodiment of a device for cleaning the hollow shaft from FIGS. 1 and 2.

DETAILED DESCRIPTION OF PREFERRED EMBODIMENTS

Figure 4:
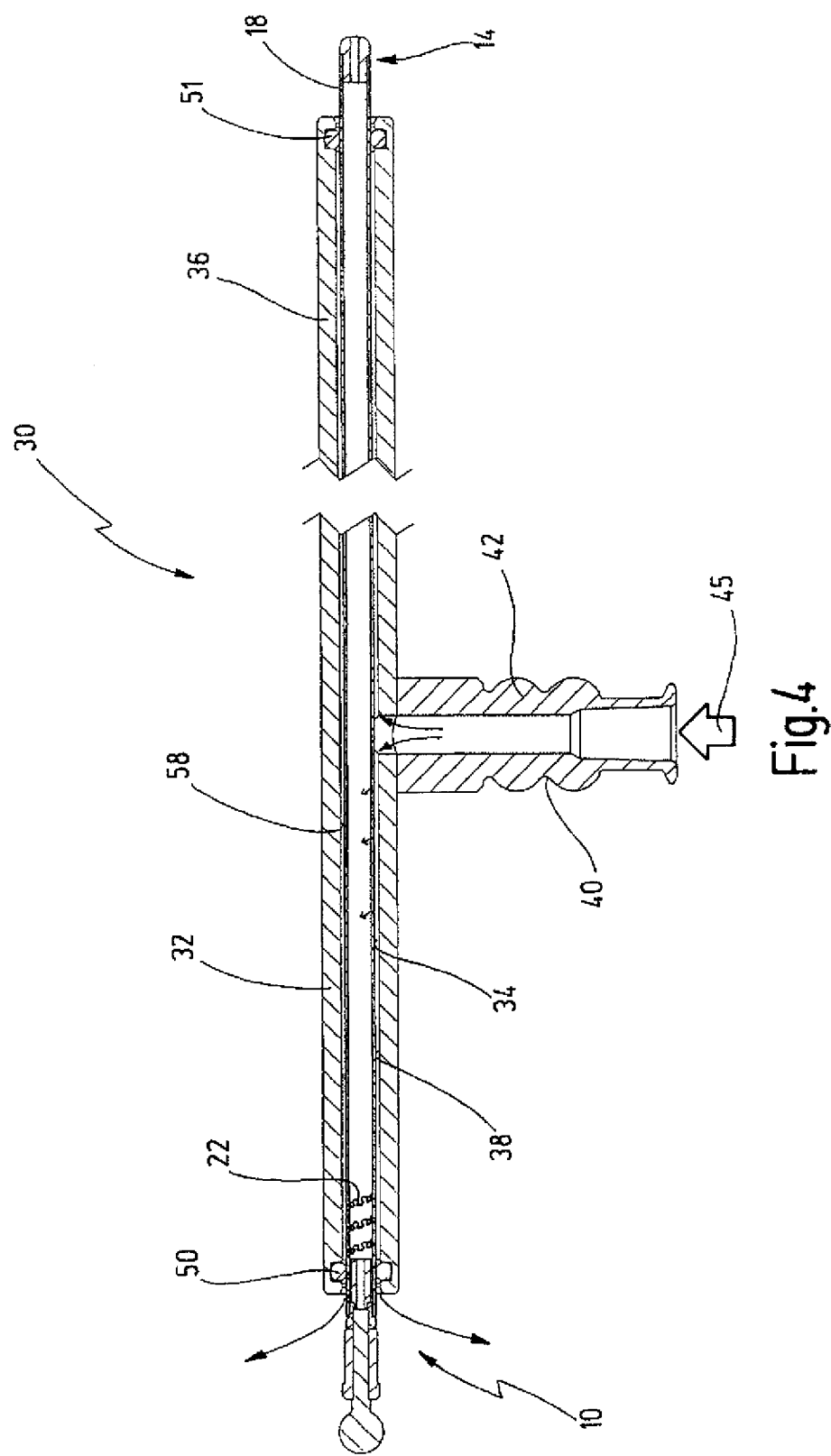
FIG. 4 shows a cross section comparable to FIGS. 2 and 3, with the hollow shaft from FIG. 2 having been inserted into the cleaning device from FIG. 3.

A hollow shaft shown in FIGS. 1 and 2 is designated overall by reference number 10.

The hollow shaft 10 has a distal end 12 and a proximal end 14. The hollow shaft 10 is designed as a tube 16 which extends between distal end 12 and proximal end 14 and is fixedly connected to these.

Numerous openings 20 are provided in the wall 18 of the tube 16.

In the illustrative embodiment shown, the openings 20 are designed as a meandering slit 22 which winds its way in a helical formation more or less from the distal end 12 to the proximal end 14 (only part of the slit is shown in the figures). By means of this slit 22, the tube 16 is flexible about axes perpendicular to its longitudinal axis, but at the same time can transmit rotation forces about its longitudinal axis. Arranged at the distal end 12 there is a tool 24 which is designed as a milling head 26. At the proximal end 14, a coupling 28 is provided which can be plugged into a rotary drive mechanism of a surgical instrument (not shown here).

The construction and mode of operation of such a surgical instrument with a flexible hollow shaft, which is received so as to rotate in a curved shank of the surgical instrument, is described in particular in document EP 0,986,989 A1, to which reference is expressly made here. The hollow shaft 10 extends almost as far as the limit stop 15 (see FIG. 1) in the inside of a curved shank of the surgical instrument, and only the milling head 26 protrudes at the distal end.

During use, contaminant material such as blood, tissue fluid or fine bone material can pass through the slits 22 into the interior of the hollow shaft 10, with the result that appropriate cleaning is necessary after a surgical intervention.

The cleaning device according to the invention, designated overall by reference number 30 in FIG. 3, is provided for this purpose.

The device 30 comprises a body 32 which has an inner hollow space 34. The body 32 comprises a hollow cylinder 36 which has a corresponding cylindrical inside wall 38.

A cleaning liquid, for example, can be passed into the hollow space 34 via a central attachment piece 40 protruding at right angles from the side, as will be described in greater detail below in connection with FIG. 4.

The attachment piece 40 is designed as a laterally protruding nozzle 42 which is provided at its outer end with what is called a Luer lock 44. A suitable syringe with a cleaning liquid, or a device with a means for delivery of a cleaning liquid, can be attached to this Luer lock 44. At the opposite end areas of the hollow cylinder 36, sealing means 48, 49 in the form of O-rings 50 and 51, respectively, are provided which are fitted into internal grooves 52 and 53, respectively. The internal diameter 46 of the hollow cylinder 36 is dimensioned such that it is greater than the external diameter 17 of the hollow shaft 10 shown in FIG. 1.

The clear internal diameter 56 of the O-rings 50, 51 is dimensioned such that it is slightly smaller than the external diameter 17 of the hollow shaft 10, but it is nevertheless dimensioned such that the hollow shaft 10 can be pushed through the O-rings 50, 51.

The O-rings 50, 51 are designed such that, when the hollow shaft 10 is inserted, as will be described below in connection with FIGS. 4 and 5, the annular space 58 extending between the outer face 19 of the hollow shaft 10 and the inside wall 38 of the hollow cylinder 36 is sealed off in the axial direction, as can be seen from FIGS. 4 and 5.

FIG. 4 shows how the hollow shaft 10 has been pushed from the left-hand end into the hollow cylinder 36 until the proximal end 14 protrudes from the right-hand end of the hollow cylinder 36 in the view in FIG. 4.

The axial distance 54 separating the two O-rings 50, 51 from one another (see FIG. 3) is of such dimension that it corresponds approximately to the total lengthwise extent of the tube 16 of the hollow shaft 10 provided with the meandering slit 22; however, this distance 54 is slightly smaller. If, as is shown in FIG. 4, a cleaning liquid 45 is now delivered via the nozzle 42, this cleaning liquid 45 distributes itself uniformly, as indicated by the flow arrows, in the annular space 58 between the inside wall 38 of the hollow cylinder 36 and the outer face 19 of the hollow shaft 10. This annular space 58 is sealed off in the axial direction by the O-rings 50, 51. The O-rings 50, 51 provide flow resistance means delimiting a flow of cleaning agent axially beyond the O-rings 50, 51 to zero.

Figure 5:
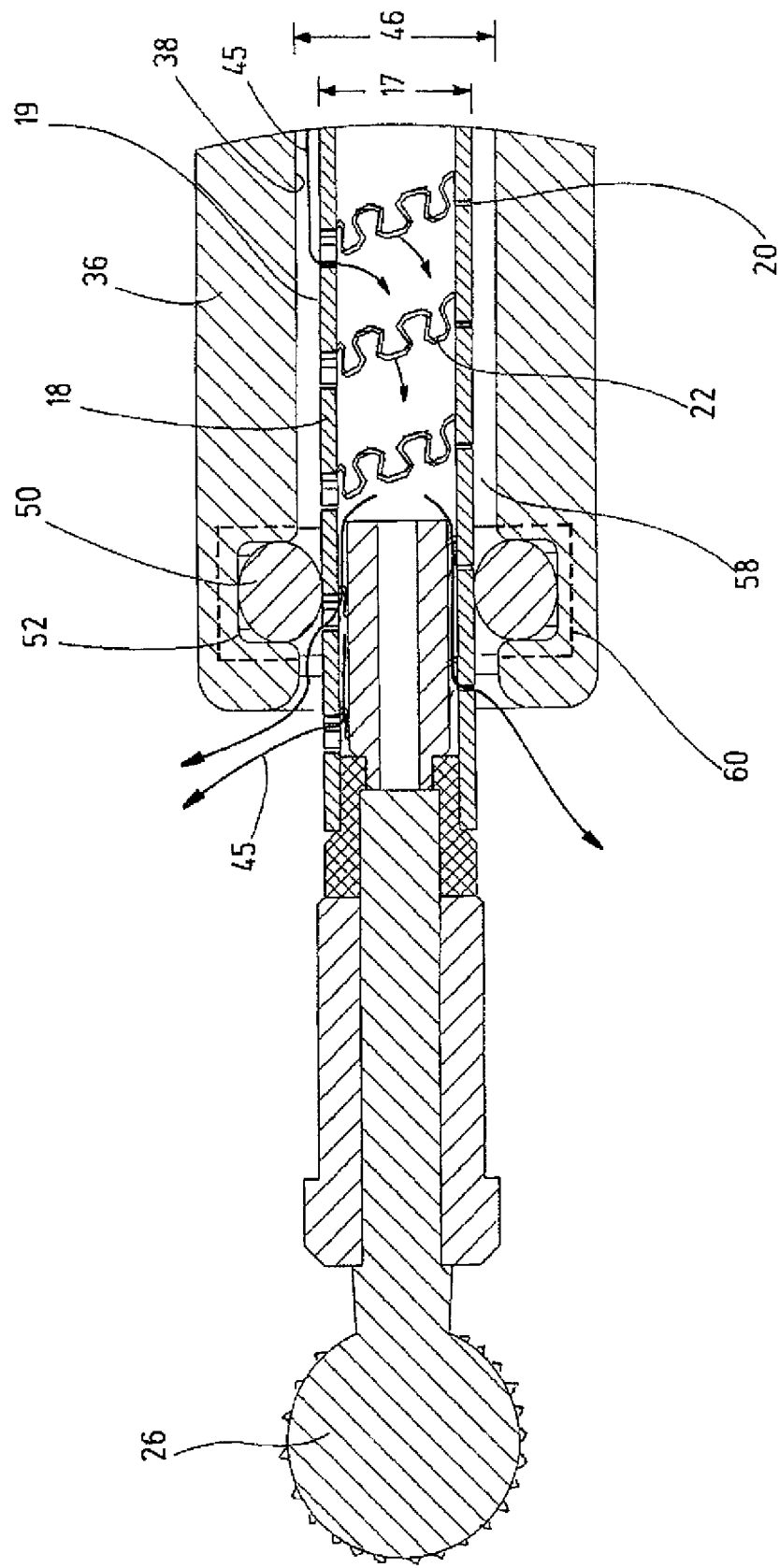
FIG. 5 shows a greatly enlarged detail of the left-hand end of the cross section from FIG. 4.

As will be seen in particular from the enlarged view in FIG. 5, the pressurized cleaning liquid 45 flows along the outer face of the hollow shaft 10, with the result that contaminant material adhering to the latter can be flushed off. The cleaning liquid 45 can then pass through the numerous openings 20, i.e. the meandering slit 22, into the interior of the hollow shaft 10, as is indicated by the flow arrows. In this way, these openings 20 are cleaned. The cleaning liquid 45 then flows through the interior of the hollow shaft 10 to the opposite ends and escapes there via openings 20 in the hollow shaft 10 or via the areas of the slit 22 outside the O-rings.

As will be seen from the enlarged view in FIG. 5, these outlet openings for escape of the cleaning liquid consist of that end portion of the meandering slit 22 located axially outside the location sealed by the O-ring 50.

However, provision can also be made for very specifically oriented outlet bores to be provided in the hollow shaft 10 in order to allow the cleaning liquid to escape at specifically defined locations.

It will be seen from FIG. 4 that a "stationary" type of cleaning is performed here, i.e. the length of the hollow cylinder 36 corresponds approximately to the length of the slotted tube 16 of the hollow shaft 10.

If the hollow shaft 10 is considerably longer, or if the length of the hollow cylinder 36 is considerably shorter, cleaning can nevertheless still be performed, for which purpose a relative displacement between hollow shaft 10 and device 30 is necessary.

This relative displacement can now be effected either by the hollow shaft 10 being moved relative to the hollow cylinder 36, or by the body 32 being moved over the hollow shaft 10. Both movements can also be performed in synchrony.

FIG. 5 shows a further variant, namely where the O-ring 50, and if appropriate also the opposite O-ring 51, is received in a displaceable bearing bushing 60. By means of this configuration, the respective sealing means, for example the O-ring 50, can be displaced axially along the hollow cylinder 36, for which purpose corresponding recesses or a movement track for the O-ring are formed on the inside face 36 of the hollow cylinder.

This displacement of the bearing bushing 60 can be performed from the outside by the operator, for example in order to bring the two O-rings 50, 51 and the corresponding bearing bushing 60 very close to the nozzle 42. The pressure of the delivered cleaning liquid 45 then causes the bearing bushings 60 to be moved away from one another as far as an axial end position, corresponding to the view in FIG. 5 for example.

The bearing bushings 60 can be not only displaceable, they can also be fixed in position, such that the annular space 58 can be adjusted to any desired axial size. This may be desirable if, for example, only a certain pressure of the cleaning liquid can be provided that is sufficient only to adequately flush a certain lengthwise section of the hollow shaft 10. This depends on how great the diameter is and how wide the slits, i.e. the openings, and on their geometry, that is to say how the flow resistance is configured.

This shows the flexibility of the device according to the invention.

In the aforementioned examples, the hollow cylinder 36 was in each case straight.

It is also possible for the hollow cylinder 36 to be curved, and the flexible hollow shaft 10 can then also be inserted into such a curved hollow cylinder 36. In this case, the respective slits would be spread wider on the outer circumference of the curve, such that they would offer a lesser degree of flow resistance to the incoming cleaning liquid 45. However, it then has to be ensured that the hollow shaft 10 is rotated in the device, so as to afford uniform flushing through of the slits.

Figure 6:
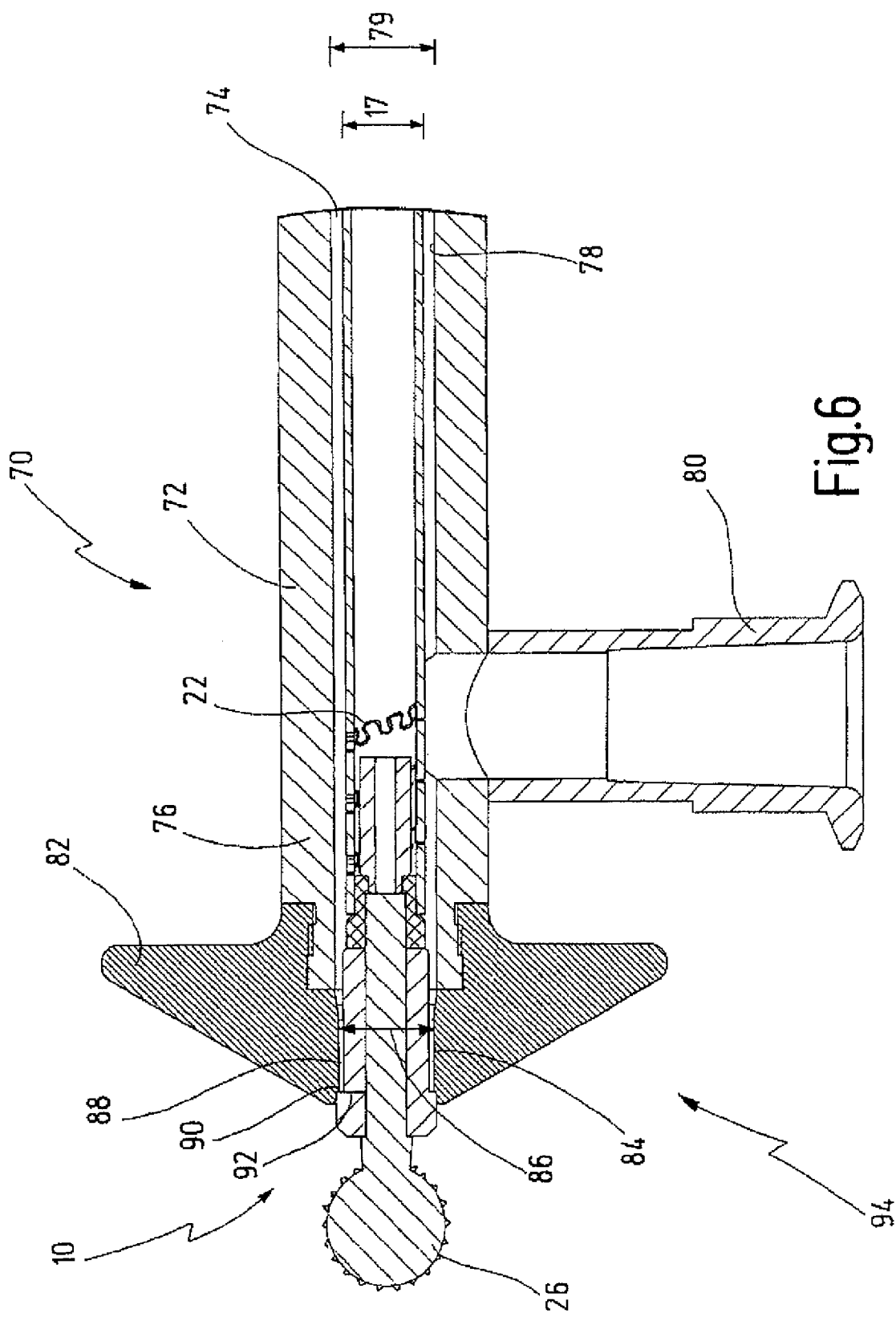
FIG. 6 shows a view, comparable to the view in FIG. 5, of another illustrative embodiment of a device which has annular gaps and in which a hollow shaft from FIG. 1 is inserted.

FIG. 6 shows another illustrative embodiment of a device according to the invention for cleaning a hollow shaft, the device being designated in its entirety by reference number 70.

The enlarged cross section shown in FIG. 6 corresponds to a left-hand end area of the device, as is shown in FIG. 5. The device 70 similarly comprises a body 72 in the interior of which a hollow space 74 is present. As has been described before, the body 72 is designed as a hollow cylinder 76. A cap 82 with a central through-opening 84 is screwed onto the left-hand end in the view in FIG. 6. This opening 84 represents a continuation of the hollow space 74 in the body 72 of the device 70.

The body 72 is provided with a laterally protruding attachment piece 80 for delivery of a cleaning liquid. In this illustrative embodiment, the attachment piece 80 is not arranged approximately centrally along the length of the body 72, but instead directly in the area of the end thereof shown in FIG. 6.

The diameter 79 of the inside wall 78 is, as has been described above, greater than the external diameter 17 of the hollow shaft 10 inserted into the hollow space 74. Therefore, as has been described above, cleaning liquid introduced via the attachment piece 80 is able to distribute itself in the space between the outer face of the hollow shaft 10 and the inside wall 78, pass radially inward through the meandering slits 22 in the wall of the hollow shaft 10, and thereby clean the latter.

The diameter 86 of the opening 84 in the cap 82 is now dimensioned such that it is slightly greater (by fractions of a millimeter) than the external diameter 17 of the hollow shaft 10, but smaller than the internal diameter 79 of the hollow space 74.

A narrowed annular gap 88 is thus created all around the outer face of the hollow shaft 10 in the area of the cap 82.

This affords the possibility that cleaning liquid, flowing across the outer face of the hollow shaft 10, can flow through this annular gap 88 to the outside. The narrowed annular gaps 88 provide flow resistance means limiting a flow of cleaning fluid in an axial direction beyond the gaps 88.

To ensure that this takes place in a precisely defined manner, a limit stop 90 is provided in the cap 82, and a corresponding abutment flange 92 of the hollow shaft 10 can come to lie on this limit stop 90. Either the limit stop 90 or the abutment flange 92 is provided with axial notches, as a result of which defined outlet openings for the cleaning liquid are created in order to allow the latter to flow from the annular gap 88 to the outside. During the cleaning procedure, a certain amount of cleaning liquid is now able to flow in the axial direction along the annular gap 88 toward the outside, and in so doing can clean the outer face. This liquid to be cleaned can then escape between the limit stop 90 and the abutment flange 92 through said notches or outlet openings. In this way, the entire outer face can be cleaned, even in the area of the flow resistance means, that is to say of the annular gap 88.

FIG. 6 shows a first end 94 of the device 70, here the left-hand end. The design of the end remote from this one is described below in connection with FIGS. 8 and 9 since this design is identical to that of the further embodiment described below with reference to FIG. 7.

Figure 7:
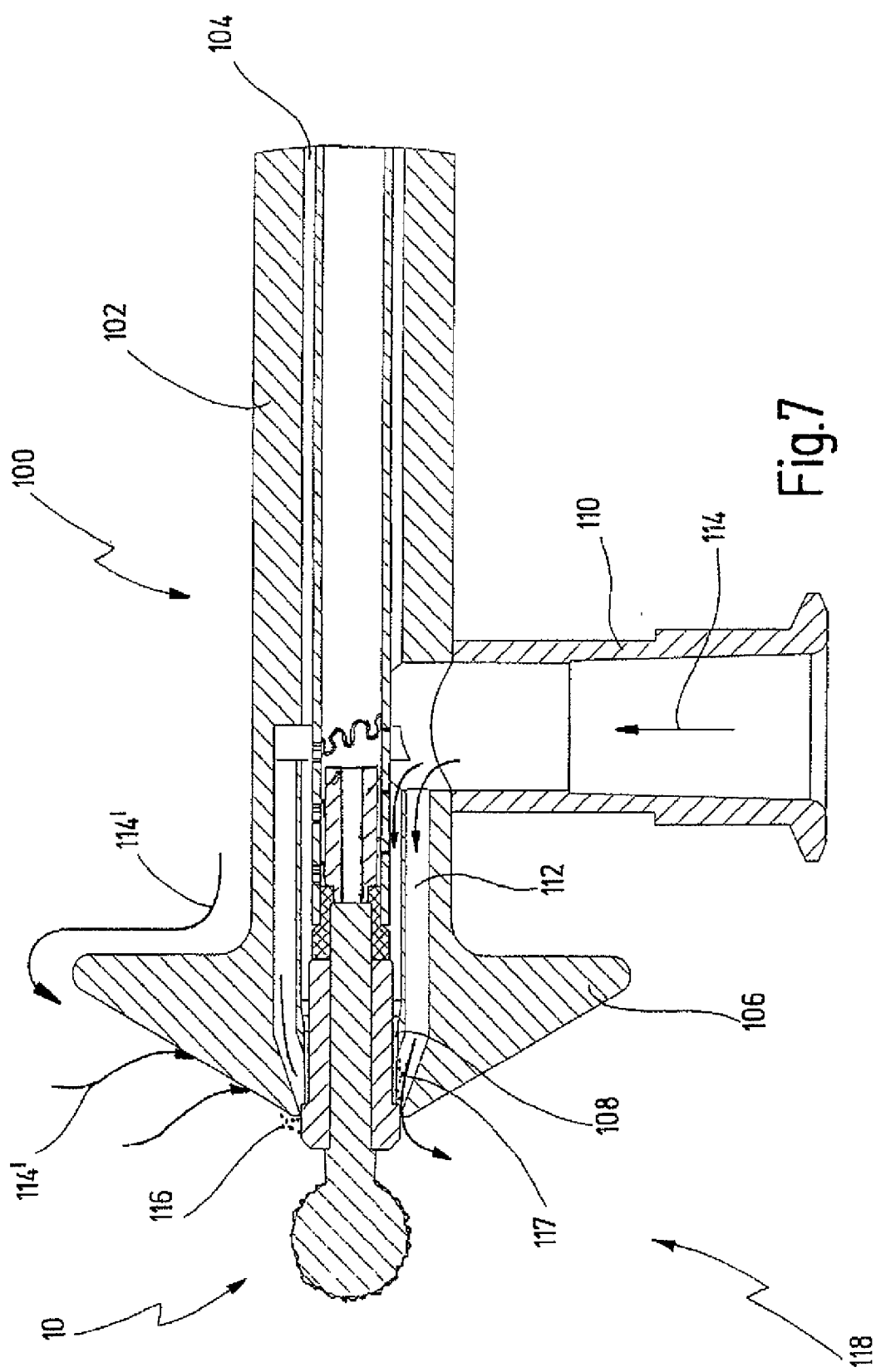
FIG. 7 shows a view, comparable to the view in FIG. 6, of another illustrative embodiment with a bypass for the cleaning liquid.

In the further embodiment described in FIG. 7, the device is designated in its entirety by reference number 100.

As has been described before in connection with FIG. 6, the device 100 has a body 102 in whose interior a hollow space 104 is present. The body 102 is provided at one end with an integral cap 106 which is designed in the same way as the cap 82 described before in connection with FIG. 6. Thus, an annular gap 108 is again present between the outer face of a hollow shaft 10, inserted into the body 102, in the area of the cap 106, via which annular gap 108 cleaning liquid 114 delivered via a nozzle 110 is able to flow out axially. When a hollow shaft 10 provided with contaminants on its outer face is inserted into the device 100, it is not possible to rule out the possibility that some of the contaminants 117 will be introduced into the interior of the annular gap 108. A considerable proportion of the contaminants 116 adhering to the outer face of the hollow shaft 10 accumulates in the area of the location indicated, they are stripped leftward along the length of the hollow shaft and lie there as a peripheral ring of contaminants 116.

To be able to remove these contaminants 117 and 116, the following measures are provided.

First, in the interior of the body 102, a bypass line 112 is provided which branches off from the attachment piece 110 and opens out in the area of the annular gap 108. Cleaning liquid 114 can now be delivered in a very targeted manner to this critical site by way of the bypass 112, and these contaminants 117 that have accumulated in the area of the annular gap can be flushed off to the outside in a defined manner, as is indicated by a flow arrow. These contaminants 117 can be ones that have originally been introduced during insertion of the hollow shaft, or they can also be contaminants that have been transported in the axial direction, by the cleaning liquid, along the outside in the direction of the annular gap 108 during the cleaning procedure.

With the cap 106 or cap 82 designed like a mushroom cap or truncated cone, liquid-conveying features are created on the outside of the device 70 or 100, by means of which it is possible to deliver cleaning liquid 114' in a targeted manner to the critical area in which the contaminants 116 have accumulated.

As has been mentioned, the device 100 is usually supplied with cleaning liquid 114 not just in the interior via the attachment piece 80 or 110, but also on its outside, for example with washing liquid 114' delivered from a fully automatic washing machine. This washing liquid 114' delivered from outside is now delivered in a targeted manner to the critical site and flushes these contaminants 116 away too. By means of the relatively large surface areas, the amount of liquid is also increased.

Figure 8:
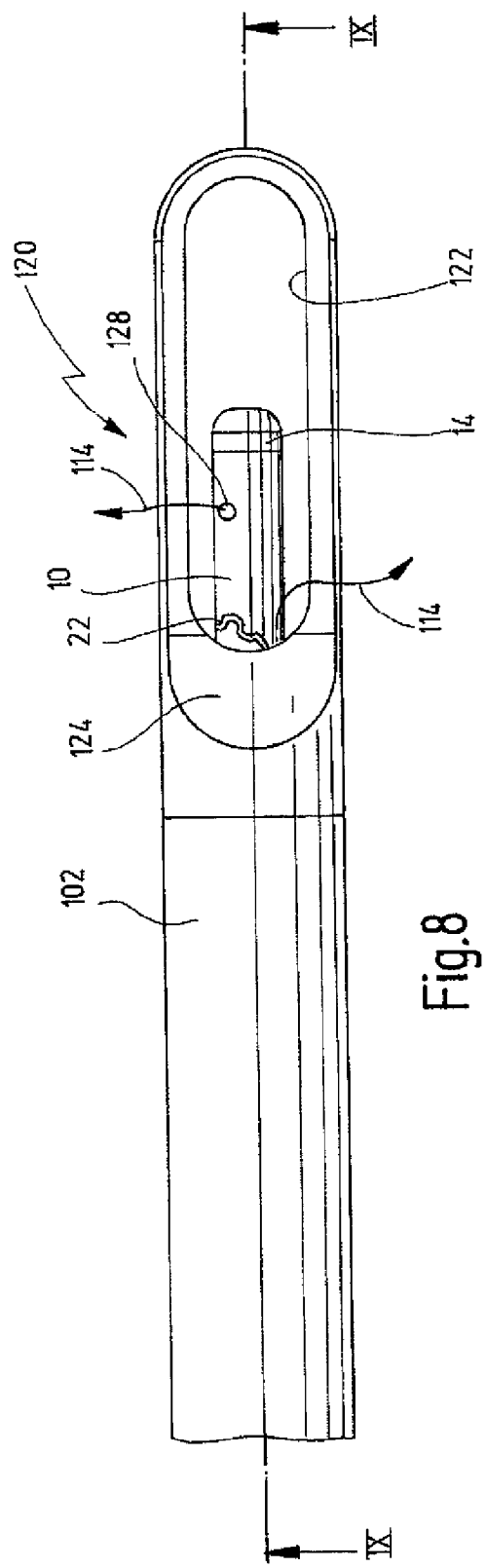
FIG. 8 shows a plan view of an opposite end area of the variants shown in FIG. 6 and/or FIG. 7.
Figure 9:
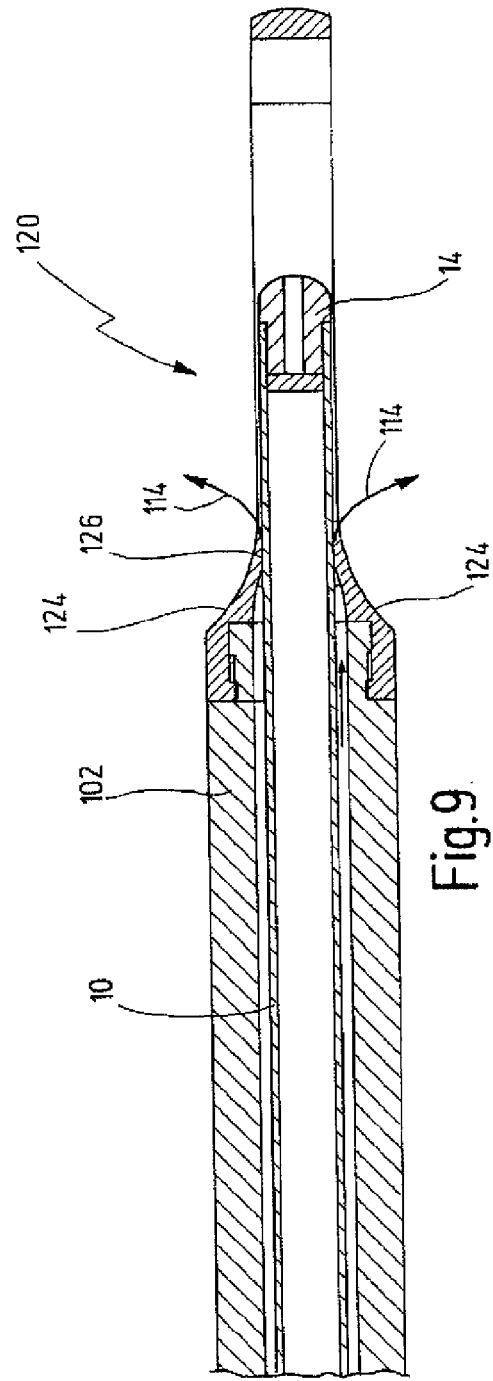
FIG. 9 shows a cross section along the line IX-IX in FIG. 8.

FIGS. 8 and 9 show the second end 120 of the devices 70 and 100 whose first ends 94 and 118 are shown in FIGS. 6 and 7, respectively.

In both devices 70 and 100, this second end is designed the same way.

It will be seen from FIG. 8 that the body is provided at each second end 120 with an opening 122 which is in the form of an eye of a needle and into which the body 102 merges via a tapering formation 124 on both sides.

In the area of the tapering formation 124, an annular gap 126 exists around the outer face of the inserted hollow shaft 120, and cleaning liquid 114 can escape through this annular gap 126, as is indicated by the flow arrows.

The design of the annular gap 126 is similar to the annular gaps 88 and 108, such that, in this case too, a continuous flushing of the outer face of the hollow shaft 10 can take place in this area of the flow resistance means.

If parts of the meandering slit 22 still lie at the proximal end 14 of the hollow shaft 10 which terminates in the area of the opening 122, cleaning liquid can pass through this slit 22 from the inside of the hollow shaft 10. However, this can also take place via an extra outlet opening 128 provided at the proximal end 14 of the hollow shaft 10, such that a quite specific outlet opening is present through which cleaning liquid 114 can escape.

The embodiments described in FIGS. 6 through 9 each involve devices, or their bodies 72 and 102, that extend in a straight line.

It is also possible, in principle, for the body to have a curved design and, if appropriate, for the hollow shaft to be rotated in the body. This may be desirable if there is a danger that wedge-shaped particles have become caught in the meandering slit 22 and cannot be entrained by the cleaning liquid entering radially from outside into the hollow shaft. As has been mentioned before, the curvature and the rotation can result in a brief widening of the slits in the outer area of curvature, such that these solid particles are then flushed inward and are conveyed centrally through an opening 128, as is shown in FIG. 8. Since the proximal end 14 lies exposed in the opening 122, all the contaminants can be flushed off continuously, for example if the device, as described above, is received in a washing/flushing machine from which not only the inside of the device is supplied with cleaning liquid, but also its outside. Depending on the design, several such devices can then of course be operated simultaneously and supplied with cleaning liquid.

Figure 10:
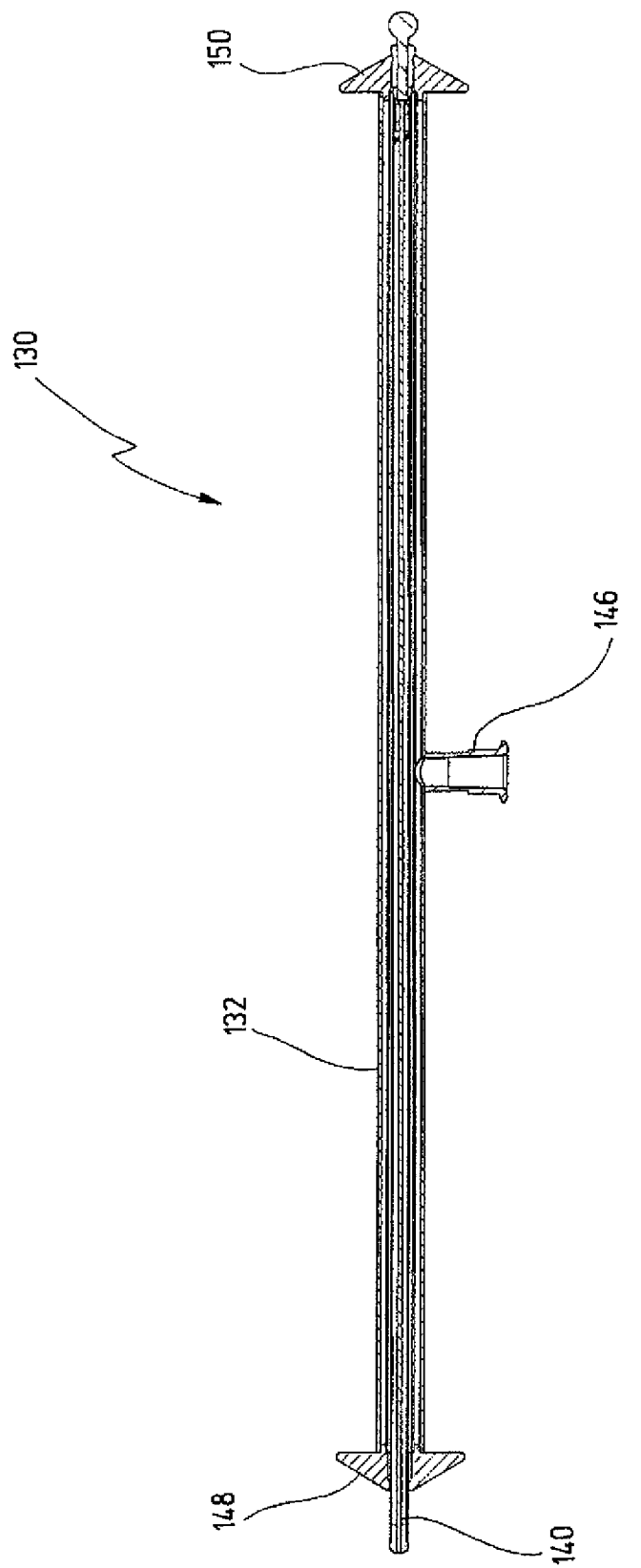
FIG. 10 shows a longitudinal section of another illustrative embodiment of a device according to the invention in which a hollow shaft is inserted.
Figure 11:
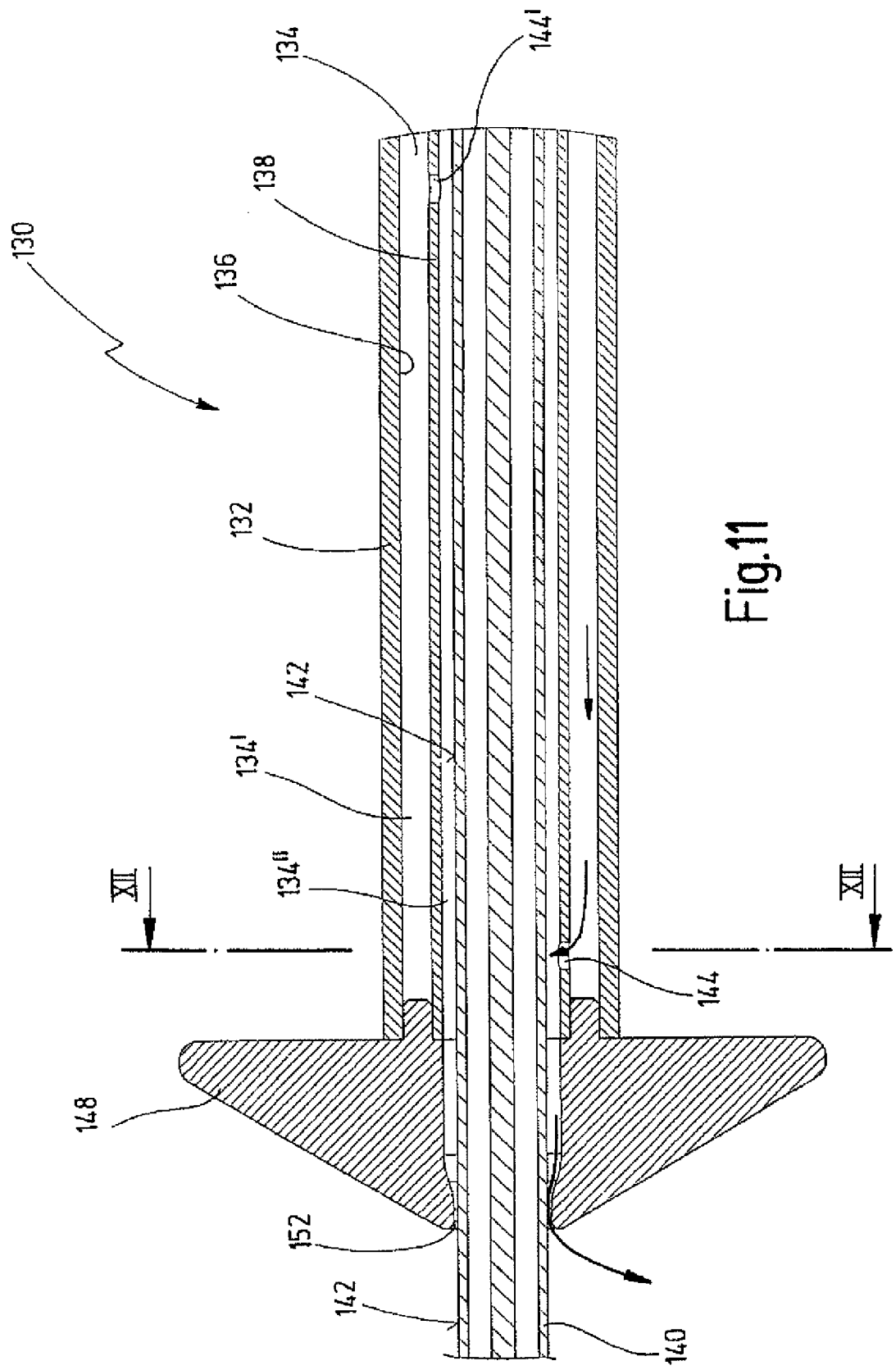
FIG. 11 shows a greatly enlarged cross-sectional view of the left-hand end area of the section from FIG. 10.
Figure 12:
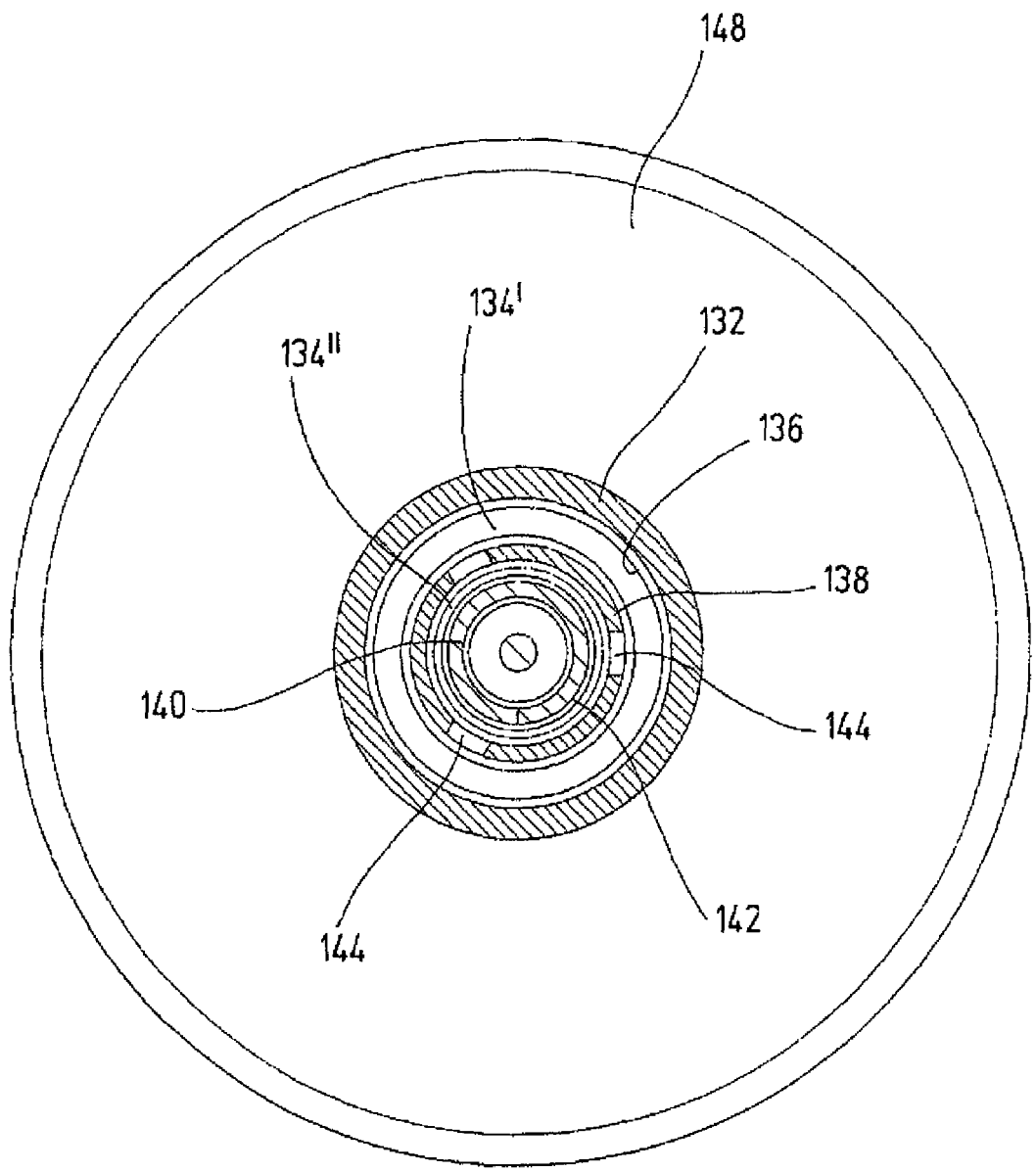
FIG. 12 shows a cross section along the line XII-XII in FIG. 11.

In another illustrative embodiment of a device 130 according to the invention shown in FIGS. 10 to 12, it similarly comprises an elongate, rectilinear, hollow-cylindrical body 132, at both ends of which caps 148 and 150, respectively, are arranged. In contrast to the previously described embodiments, the hollow space 134 contains in addition a tubular or hollow-cylindrical partition wall 138. The outer face of the partition wall 138 is located at a distance from the inside wall 136 of the hollow space 134.

The clear internal diameter of the partition wall 138 is greater than the external diameter of the hollow shaft 140. The outer face 142 of the hollow shaft 140 is thus situated at a radial distance from the partition wall 138.

The partition wall 138 thus divides the hollow space 134 into an outer hollow space 134' and an inner hollow space 134". Numerous through-openings 144 are formed in the partition wall 138.

When the cleaning agent, for example a cleaning liquid, is delivered to the attachment piece 146 as described above, it first flows into the outer area 134' of the hollow space 134 and distributes itself uniformly therein. The cleaning liquid passes through the openings 144 into the inner area 134" of the hollow space 134. From there, the cleaning liquid can then pass through the above-described meandering slit into the interior of the hollow shaft 140.

As has already been described above in connection with the embodiments in FIGS. 6 and 7, a narrow gap 152 through which cleaning liquid can escape is provided in the end area of the caps 148 and 150 leading to the outside 142 of the hollow shaft 140.

In the end area of the partition wall 138 in particular, openings 144 are arranged so as to ensure that this area specifically is supplied with cleaning agent at a sufficient pressure.

What is claimed is:

1. A combination of a flexible hollow shaft for a medical instrument and a device for cleaning said flexible hollow shaft, said combination comprising:
    a body having an inner hollow space,
    a flexible hollow shaft to be cleaned, said hollow shaft entirely passing through said hollow space;
    an attachment piece arranged at said body, a cleaning agent can be delivered through said attachment piece into said hollow space;
    said hollow shaft comprising:
    a proximal end;
    a distal end
    an interior; and
    a wall, which is provided with openings;
    wherein an inside wall of said hollow space is at a radial distance from an outer face of said hollow shaft inserted into said hollow space of said body, and wherein
    at least two flow restrictors which are axially spaced apart from one another are provided which extend in a radial direction from an inner side of said hollow space, said at least two flow restrictors delimiting a space between said outer face of said hollow shaft and said inside wall of said hollow space in axial directions, and restrict a flow of said cleaning agent in axial directions of said hollow space, said at least two flow restrictors ending at a radial distance from an outer side of said flexible hollow shaft inserted through said hollow space and an inner surface end of each flow restrictor, said radial distance being such that at least parts of said inserted cleaning agent inserted under pressure passes radially through said openings and into said interior of said hollow shaft, thereby cleaning said openings and said interior of said hollow shaft at the same time, and
    said proximal end and said distal end of said hollow shaft protruding out of said hollow space such that the cleaning agent flows through the interior of said hollow shaft and escapes from at least one of said proximal end and said distal end of said hollow shaft.

2. The device of claim 1, wherein said body is designed as a hollow cylinder.

3. The device of claim 1, wherein said body extends in a straight line.

4. The device of claim 1, wherein said body extends in a curved shape.

5. The device of claim 1, wherein an axial distance between said at least two flow restrictors corresponds approximately to a length of a portion of said hollow shaft provided with said openings.

6. The device of claim 1, wherein said at least two flow restrictors are designed as sealing means.

7. The device of claim 1, wherein said attachment piece is arranged approximately centrally in said body.

8. The device of claim 1, wherein said hollow shaft is displaceable relative to said body.

9. The device of claim 6, wherein an axial distance between said sealing means is variable.

10. The device of claim 6, wherein said sealing means are designed as O-rings.

11. The device of claim 6, wherein said sealing means are received in axially displaceable bearing bushings.

12. The device of claim 6, wherein said sealing means are formed as radially extending protrusions forming a restriction such that said cleaning agent is restricted from moving axially beyond said sealing means from said delimited space.

13. The device of claim 12, wherein in an area of said at least two flow restrictors an annular gap is present between said inside wall of said hollow space and said outer face of said hollow shaft, said cleaning agent can pass axially through said annular gaps.

14. The device of claim 13, wherein cleaning agent can additionally be delivered directly to said annular gaps.

15. The device of claim 14, wherein at least one bypass branching off from said attachment piece opens out in an area of said annular gaps.

16. The device of claim 12, wherein said hollow shaft to be cleaned can be introduced in said hollow space only from a first end.

17. The device of claim 16, wherein said first end is provided with a limit stop onto which a corresponding abutment of said hollow shaft can be placed.

18. The device of claim 17, wherein a distal end of said hollow shaft comes to lie on said first end.

19. The device of claim 18, wherein said body, at a second end, lying remote from said first end, has an opening in an area of which said proximal end of said hollow shaft come to lie.

20. The device of claim 19, wherein said body is provided, at least in an area of its first end, on its outer face with liquid-conveying features by which cleaning liquid impinging on said outer face of said hollow shaft is delivered in a targeted manner to said first end.

21. The device of claim 1, wherein said hollow space contains, at a distance from its inside wall, a partition wall which lies at a distance from said outer face of said hollow shaft and through-openings are provided in said partition wall.

* * * * *